United States Patent
Seki et al.

(10) Patent No.: US 7,432,705 B2
(45) Date of Patent: Oct. 7, 2008

(54) MAGNETIC SHIELDS AND INSTRUMENTS FOR MEASURING BIOMAGNETIC FIELDS

(75) Inventors: Yusuke Seki, Tokyo (JP); Daisuke Suzuki, Kodaira (JP); Kuniomi Ogata, Hachioji (JP); Keiji Tsukada, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 329 days.

(21) Appl. No.: 10/704,743

(22) Filed: Nov. 12, 2003

(65) Prior Publication Data

US 2004/0106863 A1 Jun. 3, 2004

(30) Foreign Application Priority Data

Nov. 29, 2002 (JP) .............................. 2002-346775

(51) Int. Cl.
*G01R 33/035* (2006.01)
(52) U.S. Cl. ...................... 324/248; 505/846; 600/409
(58) Field of Classification Search ................ 324/248; 505/162, 845–846; 327/527; 326/5; 600/409
See application file for complete search history.

(56) References Cited

U.S. PATENT DOCUMENTS

| | | | | |
|---|---|---|---|---|
| 4,857,848 A | * | 8/1989 | Takechi et al. ............... 324/318 |
| 4,912,445 A | * | 3/1990 | Yamasaki et al. ............ 335/301 |
| 5,487,304 A | * | 1/1996 | Sanzari .................... 73/504.07 |
| 5,517,169 A | * | 5/1996 | Laskaris et al. ............. 335/301 |
| 5,581,223 A | * | 12/1996 | Ono et al. ................... 335/301 |

| | | | |
|---|---|---|---|
| 2003/0218872 A1 | 11/2003 | Tsukada et al. ............. 361/816 |

FOREIGN PATENT DOCUMENTS

| | | |
|---|---|---|
| JP | 4-235369 | 1/1991 |
| JP | 5-267889 | 3/1992 |
| JP | 5-337095 | 6/1992 |
| JP | 7-226598 | 2/1994 |
| JP | 7-289530 | 4/1994 |
| JP | 8-204384 | 1/1995 |
| JP | 2000-77890 | 8/1998 |
| JP | 2002-136492 | 10/2000 |
| JP | 2002-136495 | 10/2000 |

* cited by examiner

*Primary Examiner*—Bot LeDynh
(74) *Attorney, Agent, or Firm*—Reed Smith LLP; Stanley P. Fisher, Esq.; Juan Carlos A. Marquez, Esq.

(57) ABSTRACT

There is provided a magnetic shield which can shield external magnetic fields in the direction of an axis of a tubular magnetic shield and in the direction vertical to the axis. A magnetic shield has a cylindrical ferromagnetic substance 2-1 having openings on both ends and two superconducting loops housed in the respective insides of superconducting loop containers 1-1, 1-2. The superconducting loops are constructed of high critical temperature superconducting wire. The two superconducting loops have semicircle shapes and are arranged in x-direction so as to be symmetrical with respect to an axis of the cylindrical ferromagnetic substance 2-1. The superconducting loop containers 1-1, 1-2 are arranged in the insides near both open ends of the cylindrical ferromagnetic substance 2-1 with supports 20. The superconducting loops are arranged to be vertical to the axis of the cylindrical ferromagnetic substance 2-1. The superconducting loops are cooled by liquid nitrogen or a refrigerator. A lightweight, small magnetic shield having high operability can be realized.

11 Claims, 12 Drawing Sheets

MAGNETIC SHIELDS AND INSTRUMENTS FOR MEASURING BIOMAGNETIC FIELDS

This application claims foreign priority based on Japanese Patent application No. 2002-346775, filed Nov. 29, 2002, the content of which is incorporated herein by reference in its entirety.

CROSS-REFERENCE TO RELEVANT APPLICATION

The disclosure of the patent application, Ser. No. 10/442,956, Filed on May 22, 2003, pending in THE UNITED STATES Patent AND TRADEMARK OFFICE, has been incorporated by reference into the present application.

FIELD OF THE INVENTION

The present invention relates to a magnetic shield shielding environment magnetic field noise and an instrument for measuring a biomagnetic field using the same.

BACKGROUND OF THE INVENTION

A magnetic shield is used for electronic drawing equipment using an electron beam and an instrument for measuring a biomagnetic field which measures a weak magnetic field generated from a living body. In general, a magnetically shielded room is constructed as a closed room formed by fastening plates of permalloy of an Fe-Ni alloy containing 35 to 80% Ni with high permeability with bolts with no space to a box type constructional frame of aluminum or stainless. To increase the shielding factor, the plates of permalloy are multilayered. To perform, not only magnetic shield, but also electric wave shield, a wall made of an aluminum plate having a thickness of about 1 to 10 mm is provided between the permalloy layers. The magnetic shield using the permalloy requires a number of parts and heat treatment after processing.

Instead of the permalloy, there is known a magnetic shield using a magnetic shielding sheet obtained by laminating the thin film of a high-permeability soft magnetic amorphous alloy onto a polymer film (see Patent Documents 1 and 2). In the prior art, a wall is made of a material constructed of a nonmagnetic substance to laminate the magnetic shielding sheet onto the wall for constructing a magnetically shielding room or a cylindrical magnetic shield.

There is known a magnetic shielding container in which a number of annular high-permeability magnetic substances of the same type as an inner wall of the container are laminated inside the magnetic shielding container constructed of superconductors and having tubular opening parts (see Patent Document 3).

[Patent Document 1]
Japanese Patent Application Laid-Open No. 2000-077890
[Patent Document 2]
Japanese Patent Application Laid-Open No. 2002-136492
[Patent Document 3]
Japanese Patent Application Laid-Open No. Hei 7-226598

SUMMARY OF THE INVENTION

The conventional magnetically shielded room which uses multilayered permalloy must surround the entire apparatus by a ferromagnetic substance. Its volume and weight are increased to require a large installation place. The magnetically shielded room for electronic drawing equipment installed in a clean room needs, in its inside, air-conditioning equipment to increase the cost.

In a cylindrical magnetic shield with open ends, an external magnetic field penetrates from the open ends to the inside. The axial length about twice larger than its diameter is necessary, thereby imposing the problem of shortening in the axial length.

In an unpublished magnetic shield using superconducting loops, superconducting loops are provided in the opening parts of a cylindrical ferromagnetic substance to shield an axial external magnetic field by the action of the superconducting loops. However, no consideration is given to an external magnetic field vertical to the axis. The external magnetic field vertical to the axis penetrates into the cylindrical magnetic shield from the open ends. In this case, the change of the magnetic flux penetrating through the superconducting loops is 0, and no shielding current flows in the superconducting loops.

An object of the present invention is to provide a magnetic shield which can shield an external magnetic field vertical to an axis of a tubular magnetic shield with open ends on at least one end and in the direction vertical to the axis, and an instrument for measuring a biomagnetic field using the same. Another object of the present invention is to provide a relative arrangement method of a magnetic shield and an instrument for measuring a biomagnetic field, and a relative arrangement method of a magnetic shield and a measuring instrument using a charged particle beam.

The magnetic shield according to the present invention applies a characteristic that the magnetic flux through a superconducting loop is constant to shield external magnetic fields using superconducting loops. A superconducting loop is made by connecting both edge of superconducting wire. Alternatively, bulk superconductor may be used to form a superconducting loops.

The magnetic shield according to the present invention is used for an instrument for measuring a biomagnetic field which detects a weak biomagnetic field generated from a living body and a measuring instrument using a charged particle beam.

The magnetic shield according to the present invention has a cylindrical magnetic shield constructed of a ferromagnetic substance, in which a plurality of superconducting loops are arranged on a plane vertical to an axis near at least one open end in the direction of the axis of the cylindrical magnetic shield. The planes formed by the plurality of superconducting loops are vertical to the axis. A shielding current flows in the superconducting loop corresponding to the change of the total magnetic flux through the superconducting loop, which can suppress the magnetic field parallel to the axis near the open end. The cylindrical magnetic shield may be a tubular magnetic shield. In the following description, the cylinder will be taken as an example.

The magnetic shield according to the present invention can shield, not only an external magnetic field parallel to the axis, but also an external magnetic field vertical to the axis. This can reduce magnetic field noise in the cylindrical magnetic shield as compared with the case that there is one superconducting loop at each open end. It is possible to realize an open-type, small, lightweight magnetic shield.

The magnetic shield according to the present invention does not use large superconductors so that a cryostat is simple. The superconducting loops and the cylindrical magnetic shield are manufactured separately. These are combined to realize a simple construction.

An instrument for measuring a biomagnetic field according to the present invention uses the above-described magnetic shield to arrange detection coils detecting a biomagnetic field generated from a living body so that the planes of the detection coils are parallel to the axis of the cylindrical magnetic shield. That is, in a relative arrangement method of the above-described magnetic shield and the instrument for measuring a biomagnetic field according to the present invention, the detection coils are arranged on the inside of the cylindrical magnetic shield so that the planes of the detection coils are parallel to the axis of the cylindrical magnetic shield. In the instrument for measuring a biomagnetic field according to the arrangement method, a biomagnetic field can be measured at a high S/N ratio.

In a relative arrangement method of a measuring instrument using a charged particle beam and the above-described magnetic shield according to the present invention, the measuring instrument is arranged in the tubular magnetic shield so that the travel direction of a charged particle beam is parallel to the axis of the cylindrical magnetic shield. In the arrangement method, external magnetic fields parallel to and vertical to the travel direction of the charged particle beam can be shielded and the openability is high. When the instrument is installed in a clean room, independent air-conditioning equipment is unnecessary.

DESCRIPTION OF THE PREFERRED EMBODIMENT

Figure 1:
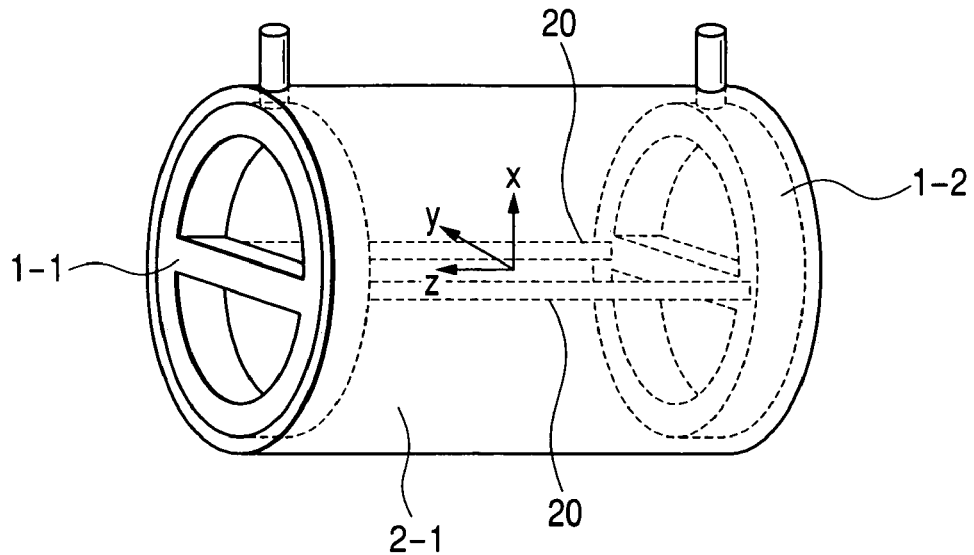
FIG. 1 is a perspective view showing the construction of a magnetic shield of Embodiment 1 of the present invention.

In a magnetic shield according to the present invention, near at least one open end of a tubular magnetic shield constructed of a ferromagnetic substance, a plurality of superconducting loops are arranged on a plane vertical to the axis. The planes formed by the plurality of superconducting loops are vertical to the axis. A plurality of tubular magnetic shields having different diameters are arranged to surround the one axis.

An instrument for measuring a biomagnetic field according to the present invention uses the above-described magnetic shield. Detection coils detecting a magnetic field generated from a living body vertical to the one axis of a magnetic shield are arranged on a tubular magnetic shield so that the planes of the detection coils are parallel to the one axis.

In a magnetic shield according to the present invention, near at least one open end of a cylindrical magnetic shield constructed of a ferromagnetic substance, a plurality of superconducting loops are arranged on a plane vertical to the axis. The planes formed by the plurality of superconducting loops are vertical to the axis. A plurality of cylindrical magnetic shields having different diameters are arranged to surround the axis. In the arrangement, the axial length of the cylindrical magnetic shield is longer as the diameter of the cylindrical magnetic shield is larger, and another plurality of the cylindrical magnetic shields are arranged in the cylindrical magnetic shield in which the diameter is largest. A mechanism which moves part of the plurality of cylindrical magnetic shields around the axis is provided to form an opening part in the circumferential direction of the plurality of cylindrical magnetic shields. Further, the plurality of superconducting loops are arranged in the inside portion of the cylindrical magnetic shield arranged on the outermost side and in the outside portion of the cylindrical magnetic shield arranged on the innermost side.

An instrument for measuring a biomagnetic field according to the present invention uses the above-described magnetic shield. A plurality of fluxmeters having SQUID and detection coils are arranged and cooled in the inside of a cryostat in one dimension or in two dimensions so that the planes of the detection coils are parallel to the axis. The cryostat is held on the inside of the cylindrical magnetic shield arranged on the innermost side by a gantry. A living body is inserted into the cylindrical magnetic shield arranged on the innermost side. A measuring circuit drives the plurality of fluxmeters to detect a magnetic field generated from the living body for outputting it as a measuring signal. An analyzer analyses the measuring signal to display the analyzed result. The plurality of superconducting loops are constructed of first and second superconducting loops having different loop areas and arranged on the side of one end of the cylindrical magnetic shield. The first superconducting loop is arranged to surround the axis. The second superconducting loop is arranged not to surround the axis. The planes formed by the first and second superconducting loops are vertical to the axis. The plurality of superconducting loops are constructed of third and fourth superconducting loops having the same loop area, arranged in the positions symmetrical with respect to the axis, and arranged on the side of the other end. The planes formed by the third and fourth superconducting loops are vertical to the axis. The above-described magnetic shield is arranged so that the direction of the axis is substantially matched with the direction horizontal to the ground or with the direction vertical to the ground.

Embodiments of the present invention will be described below in detail with reference to the drawings.

(Embodiment 1)

Figure 2:
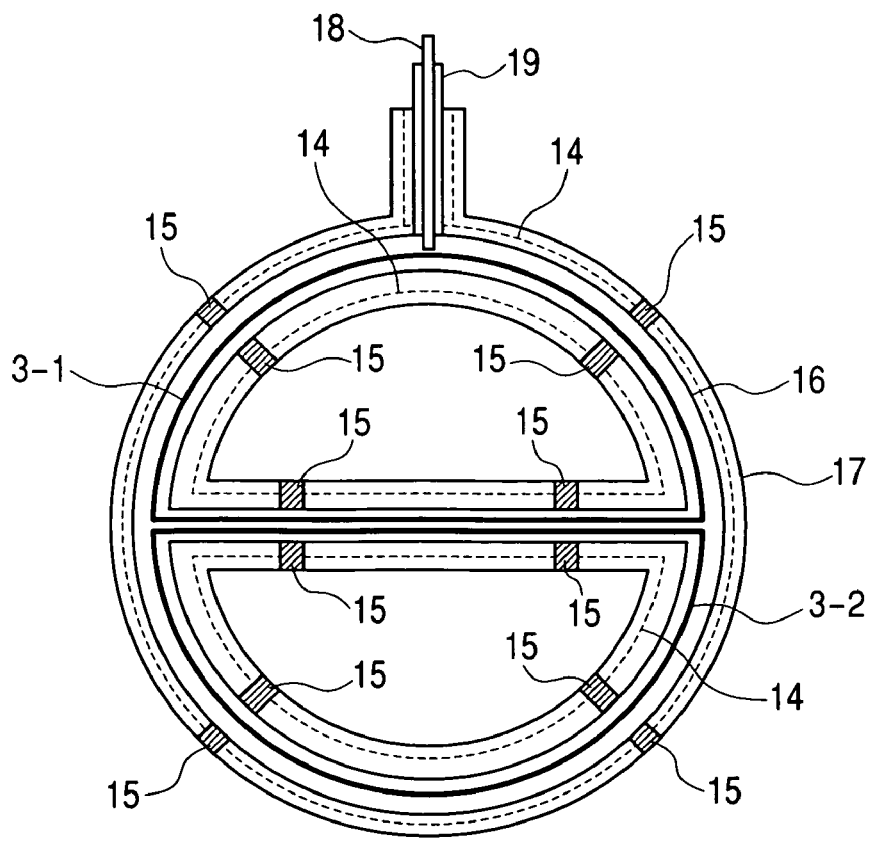
FIG. 2 is a cross-sectional view of a superconducting loop container of Embodiment 1 of the present invention.
Figure 3:
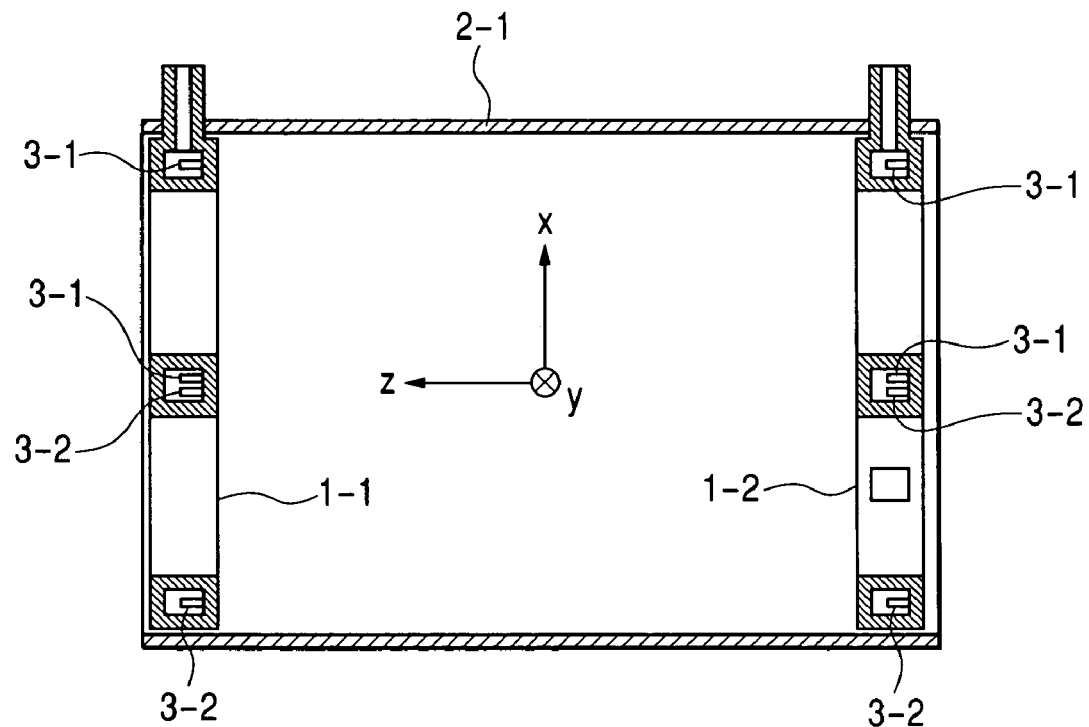
FIG. 3 is a cross-sectional view of a magnetic shield of Embodiment 1 of the present invention.

FIG. 1 is a perspective view showing the construction of a magnetic shield of Embodiment 1 of the present invention. FIG. 2 is a cross-sectional view of a superconducting loop container 1 of Embodiment 1 of the present invention and is a cross-sectional view of a plane parallel to yz shown in FIG. 1 passing through the superconducting loops. FIG. 3 is a cross-sectional view of the magnetic shield of Embodiment 1 of the present invention and is a cross-sectional view of xz-plane shown in FIG. 1.

The magnetic shield has a cylindrical ferromagnetic substance 2-1 having openings on both ends and two superconducting loops housed in the respective insides of superconducting loop containers 1-1, 1-2. The superconducting loops are constructed of high critical temperature superconducting wire. The two superconducting loops have semicircle shapes and are arranged in x-direction to be symmetrical with respect to an axis of the cylindrical ferromagnetic substance 2-1.

The superconducting loop containers 1-1, 1-2 are arranged in the insides near both open ends of the cylindrical ferromagnetic substance 2-1 with supports 20. The superconducting loop containers 1-1, 1-2 may be arranged in the outsides near both open ends of the cylindrical ferromagnetic substance 2-1 with the support 20. The superconducting loops are arranged to be vertical to the axis of the cylindrical ferromagnetic substance 2-1.

The superconducting loops constructed of high critical temperature superconducting wire are cooled by liquid nitrogen or a refrigerator. FIG. 2 shows the construction of the superconducting loop container 1 when cooling the superconducting loops by liquid nitrogen. Superconducting loops 3-1, 3-2 are housed in a pipe 16 formed of a nonmagnetic metal. The liquid nitrogen is circulated in the pipe 16 to cool the superconducting loops. Flexible thermal insulation 14 using heat radiation is wound around the pipe 16 to be multilayered, which strengthens thermal shield. The pipe 16 in which shield is thermally strengthened is arranged via spacers 15 in a dewar 17 having a pipe shape formed of a nonmagnetic metal. Liquid nitrogen is supplied into the pipe 16 from a supply pipe 18. A nitrogen gas generated in the pipe 16 is discharged from a discharge pipe 19.

When the superconducting loops are cooled using a refrigerator, a pulse tube refrigerator or a Gifford-McMahon type refrigerator is used to cool the superconducting wire below the critical temperature.

The magnetic shield of Embodiment 1 shields an external magnetic field so as to maintain the magnetic flux penetrating the loops constant with respect to the external magnetic field parallel to the axis (z-direction) of the cylindrical ferromagnetic substance 2-1. It can also effectively shield a magnetic field absorbed into the cylindrical ferromagnetic substance with respect to an external magnetic field vertical to the axis (x-direction) of the cylindrical ferromagnetic substance 2-1.

(Embodiment 2)

Figure 4:
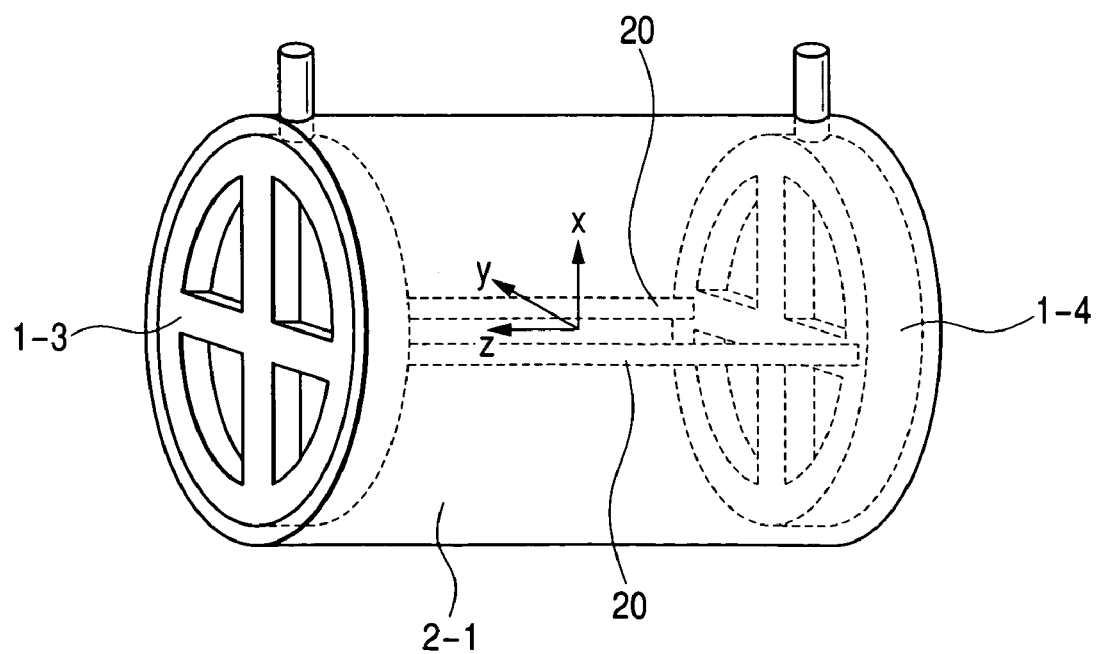
FIG. 4 is a perspective view showing the construction of a magnetic shield of Embodiment 2 of the present invention.

FIG. 4 is a perspective view showing the construction of a magnetic shield of Embodiment 2 of the present invention. The magnetic shield has a cylindrical ferromagnetic substance 2-1 having openings on both ends, and four superconducting loops housed in the respective insides of superconducting loop containers 1-3, 1-4. The superconducting loops are constructed of high critical temperature superconducting wire. The four superconducting loops have quarter circle shapes and are arranged in x and y-directions so as to be symmetrical with respect to an axis of the cylindrical ferromagnetic substance 2-1. The superconducting loop containers 1-3, 1-4 are arranged in the insides near both open ends of the cylindrical ferromagnetic substance 2-1 with supports 20. The superconducting loop containers 1-3, 1-4 may be arranged in the outsides near both open ends of the cylindrical ferromagnetic substance 2-1 with the supports 20. The superconducting loops are arranged to be vertical to the axis of the cylindrical ferromagnetic substance 2-1.

As in Embodiment 1, the superconducting loops constructed of high critical temperature superconducting wire are housed in a pipe formed of a nonmagnetic metal, liquid nitrogen is circulated in the pipe, and the superconducting loops are cooled.

The magnetic shield of Embodiment 1 shields an external magnetic field so as to maintain the magnetic flux penetrating the loops constant with respect to the external magnetic field parallel to the axis of the cylindrical ferromagnetic substance 2-1 (z-direction). It can also effectively shield a magnetic field absorbed into the cylindrical ferromagnetic substance with respect to an external magnetic field in the directions vertical to the axis of the cylindrical ferromagnetic substance 2-1 (x and y-directions).

(Embodiment 3)

A magnetic shield of Embodiment 3 of the present invention has a construction such that one or more cylindrical ferromagnetic substances are arranged on the outside of the magnetic shield of Embodiment 1 or 2.

Figure 5:
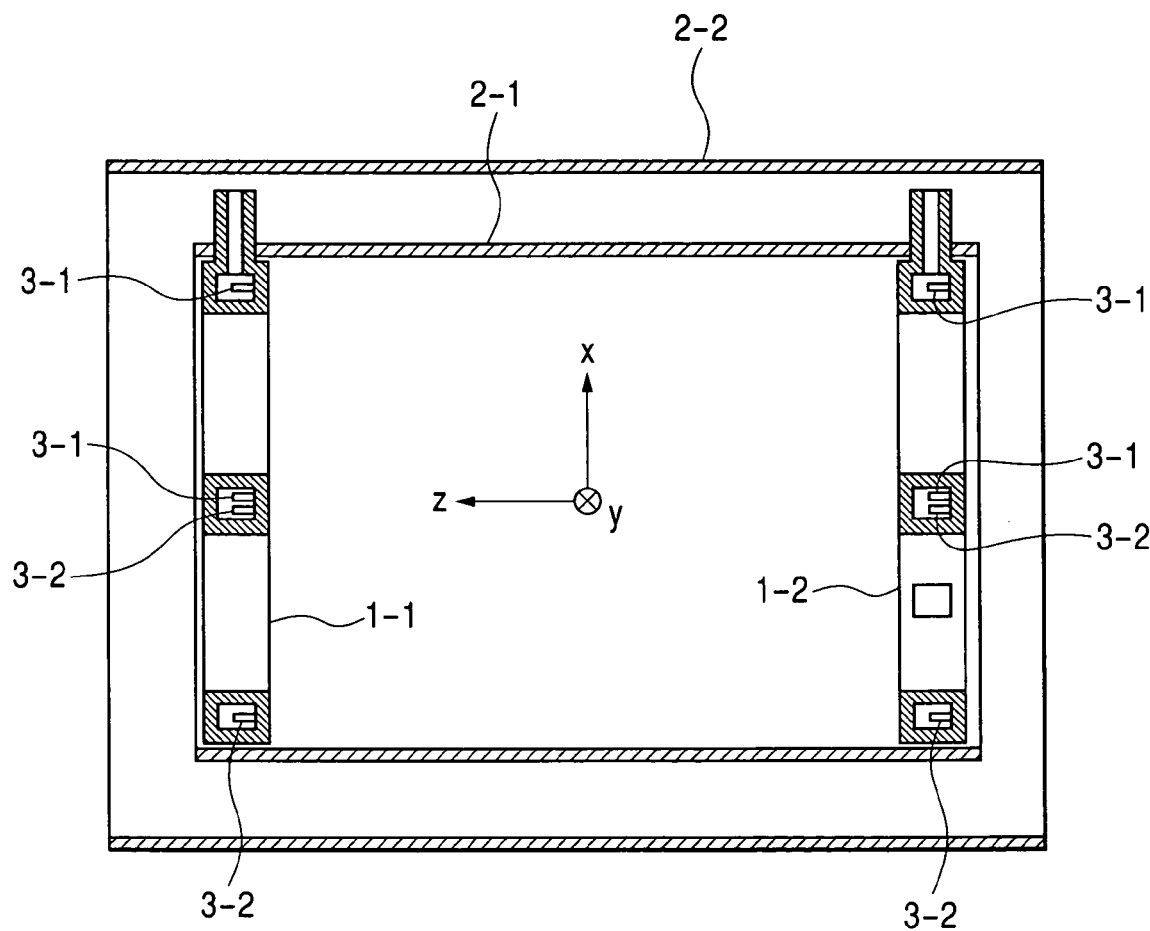
FIG. 5 is a cross-sectional view showing the construction of a magnetic shield of Embodiment 3 of the present invention.

FIG. 5 is a cross-sectional view showing the construction of a magnetic shield of Embodiment 3 of the present invention and a cross-sectional view of xz plane. In the magnetic shield of Embodiment 3, a cylindrical ferromagnetic substance 2-2 coaxial with the axis of the cylindrical ferromagnetic substance 2-1 explained in FIGS. 1, 2 and 3 is arranged on the outside of the cylindrical ferromagnetic substance 2-1. In the example shown in FIG. 5, the length in the direction of an axis of the cylindrical ferromagnetic substance 2-2 is larger than that of the cylindrical ferromagnetic substance 2-1 and may be almost the same. In addition, in the example shown in FIG. 5, one cylindrical ferromagnetic substance 2-2 having openings on both ends is used. A plurality of cylindrical ferromagnetic substances having openings of different diameters may be used.

The construction such that a plurality of cylindrical ferromagnetic substances are coaxially arranged can enhance the shield effect in the direction vertical to the axis of the cylindrical ferromagnetic substances and the shield effect in the direction parallel to the axis of the cylindrical ferromagnetic substances. The construction increases the intensity of external magnetic fields absorbed into the cylindrical ferromagnetic substances. The effect of the superconducting loops is increased.

(Embodiment 4)

FIG. 6 is a diagram showing examples of the shapes and arrangements of the superconducting loops used in the respective embodiments of the present invention. The superconducting loops are constructed of high critical temperature superconducting wire. The shapes of the superconducting loops can be arbitrary and are not limited to the examples shown in FIG. 6.

Figure 6A:
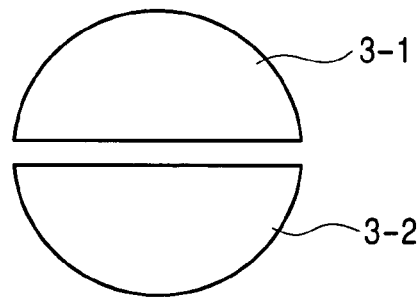
FIG. 6 is a diagram showing examples of the shapes and arrangements of superconducting loops used in the respective embodiments of the present invention.

The example shown in FIG. 6(A) shows the shape and arrangement of the superconducting loops used in Embodiment 1. Superconducting loops 3-1, 3-2 have semicircle shapes having the same area and are arranged in one direction so as to be symmetrical with respect to an axis of the cylindrical ferromagnetic substance. The superconducting loops 3-1, 3-2 are formed of one straight line part and one arc part, respectively.

Figure 6D:
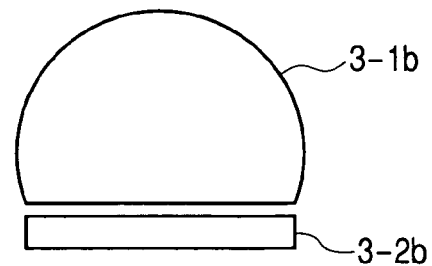
Figure 6B:
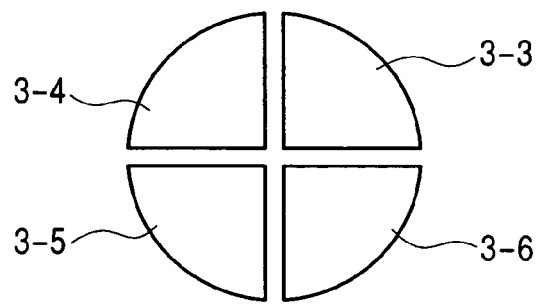

The example shown in FIG. 6(B) shows the shape and arrangement of the superconducting loops used in Embodiment 2. Superconducting loops 3-3, 3-4, 3-5 and 3-6 have quarter circle shapes having the same area and are arranged in two directions orthogonal to each other so as to be symmetrical with respect to an axis of the cylindrical ferromagnetic substance. The superconducting loops 3-3, 3-4, 3-5 and 3-6 are formed of two straight line parts and one arc part, respectively. The superconducting loops 3-3, 3-4, 3-5 and 3-6 are housed in the superconducting loop containers 1-3, 1-4 shown in FIG. 4.

Figure 6E:
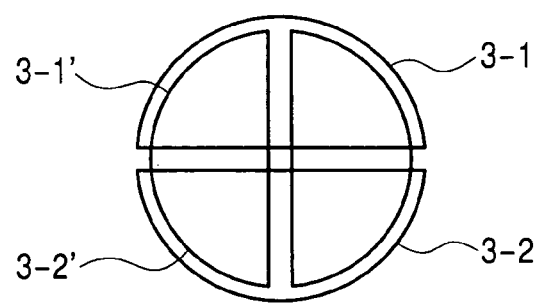
Figure 6C:
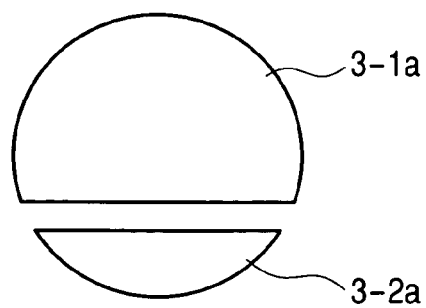

The example shown in FIG. 6(C) uses two superconducting loops 3-1a, 3-2a having different loop areas. The two superconducting loops 3-1a, 3-2a are arranged in one direction so as to be symmetrical with each other. The superconducting loop 3-1a is arranged so as to surround an axis of the cylindrical ferromagnetic substance. The superconducting loop 3-2a is arranged so as not to surround the axis thereof.

The example shown in FIG. 6(D) uses a superconducting loop 3-1b having the same shape as that of the superconducting loop 3-1a shown in FIG. 6(C) and a superconducting loop 3-2b having rectangular shapes having a small width. The two superconducting loops 3-1b, 3-2b are arranged in one direction so as to be symmetrical with each other. The superconducting loop 3-1b is arranged to surround an axis of the cylindrical ferromagnetic substance. The superconducting loop 3-2b is arranged not to surround the axis thereof.

The example shown in FIG. 6(E) uses the superconducting loops 3-1, 3-2 shown in FIG. 6(A) arranged to be overlapped with superconducting loops 3-1', 3-2' rotated 90° with respect to them. The superconducting loops 3-1, 3-2, 3-1', 3-2' are arranged in two directions orthogonal to each other so as to be symmetrical with an axis of the cylindrical ferromagnetic substance.

Figure 6F:
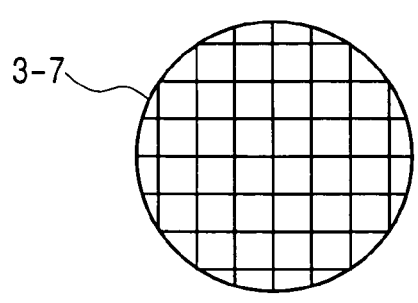

The example shown in FIG. 6(F) uses a net-like superconducting loop 3-7 constructed of a number of loops made of high critical temperature superconducting wire. The example shown in FIG. 6(F) can also use a bulk-like high critical temperature superconductor. The net-like superconducting loop or the bulk-like high critical temperature superconductor is arranged on the side of one end of the cylindrical magnetic shield.

When using the magnetic shield of the present invention in an instrument for measuring a biomagnetic field; the two superconducting loops 3-1a, 3-2a shown in FIG. 6(C) are arranged on the side of one end of the cylindrical magnetic shield. Alternatively, the two superconducting loops 3-1b, 3-2b shown in FIG. 6(D) are arranged on the side of one end of the cylindrical magnetic shield.

(Embodiment 5)

Figure 7:
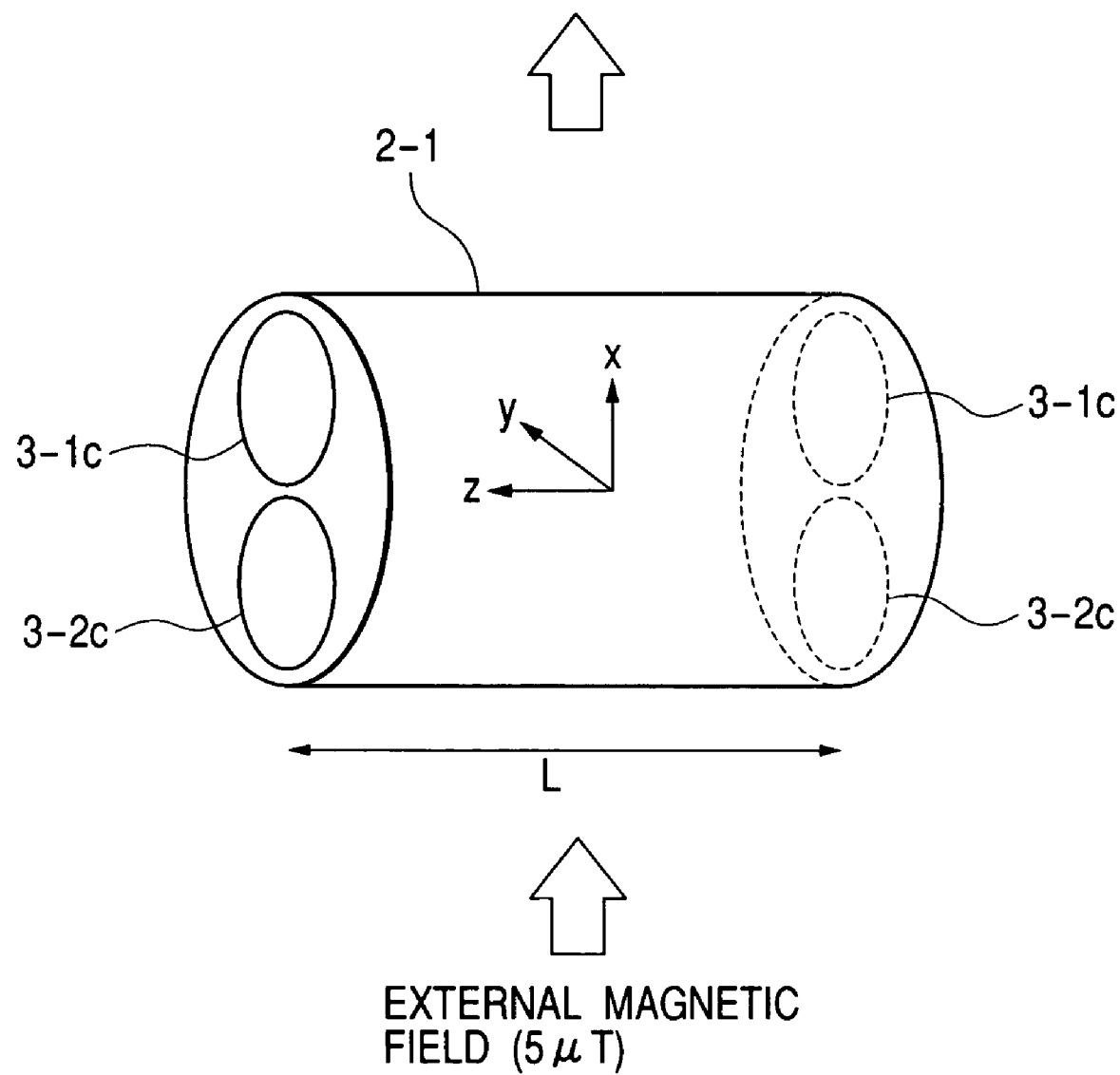
FIG. 7 is a model diagram of a magnetic shield for use in simulation analysis of Embodiment 5 of the present invention.

FIG. 7 is a model diagram of a magnetic shield used in simulation analysis in Embodiment 5 of the present invention. A cylindrical ferromagnetic substance 2-1 is constructed of a ferromagnetic substance having a relative permeability of 20000 and a thickness of 2 mm. The diameter of the cylindrical ferromagnetic substance 2-1 is 100 cm and the length in the direction of an axis is L cm. As shown in FIG. 7, on the open planes of both ends of the cylindrical ferromagnetic substance 2-1, two superconducting rings 3-1c, 3-2c having a diameter of 49.6 cm are away from each other by 0.4 cm to be arranged in the positions symmetrical with respect to the axis in the direction of an external magnetic field (x-direction). The magnitude of the external magnetic field in the x direction is 5 µT.

Figure 8:
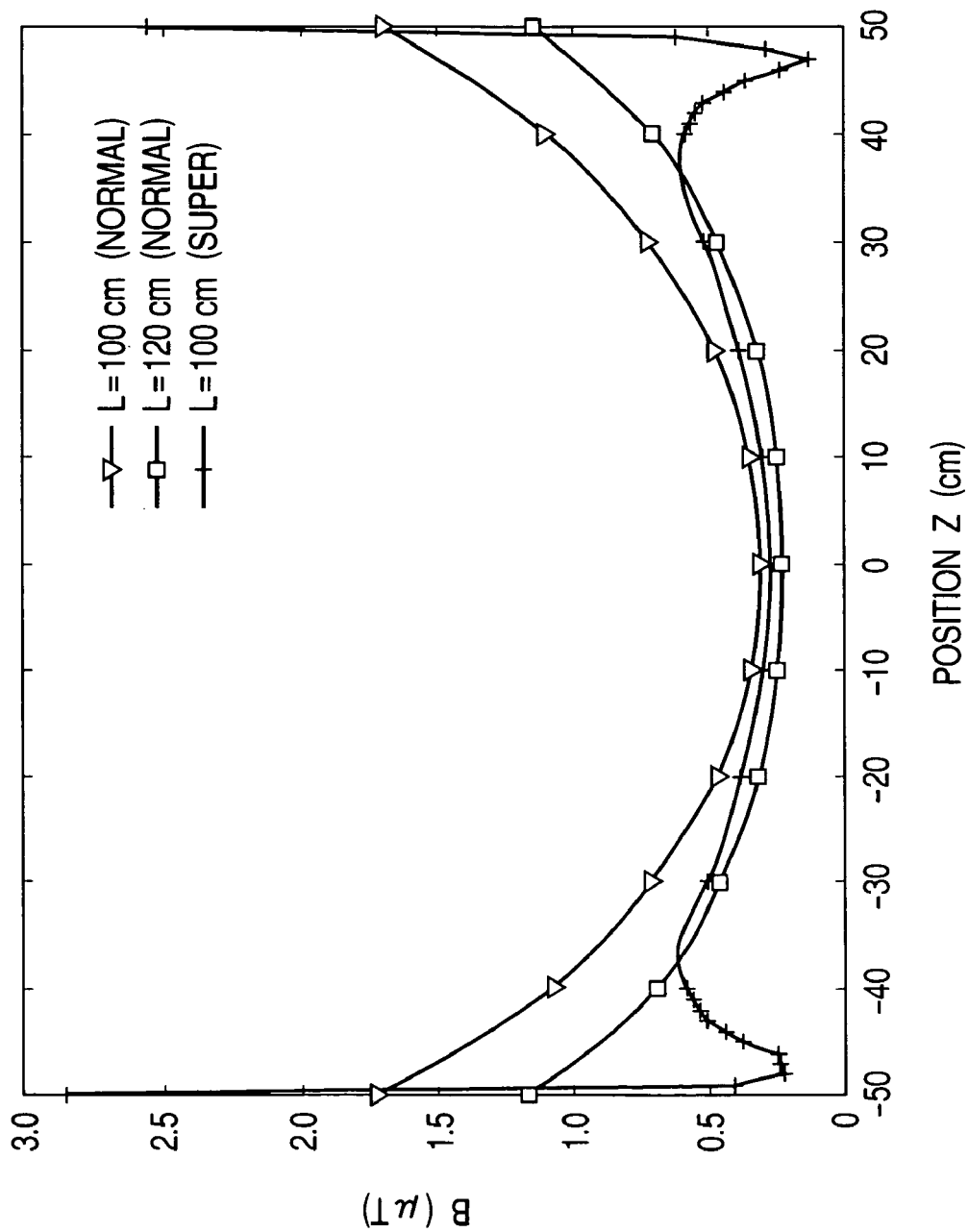
FIG. 8 is a diagram showing a result example of the simulation analysis of Embodiment 5 of the present invention.

FIG. 8 is a diagram showing a result example of the simulation analysis in Embodiment 5 of the present invention. FIG. 8 shows results in which with the center position in the direction of the axis (z-direction) of the magnetic shield shown in FIG. 7 as 0, magnitudes B (µT) of a magnetic field in x-direction in the positions on the axis (z-axis) are obtained from the simulation analysis. FIG. 8 shows, in FIG. 7, three results of (1) the case that the superconducting rings 3-1c, 3-2c are used and L=100 cm (super), (2) the case that the superconducting rings 3-1c, 3-2c are not used and L=100 cm (normal), and (3) the case that the superconducting rings 3-1c, 3-2c are not used and L=120 cm (normal).

Based on the results shown in FIG. 8, as in the (1), from the use of the superconducting rings 3-1c, 3-2c, the shielding factor in the x-direction vertical to the axis (z-axis) is found to be improved as compared with the (2), (3). In particular, the shielding factor is improved near the opening positions (z=−50 cm, +50 cm) on both ends. The shield factor is defined by 20 log {(a magnitude of an external magnetic field applied in the x-direction)/(value B of the vertical axis shown in FIG. 8)}.

From the effect of the superconducting rings 3-1c, 3-2c, the distribution of the magnitudes B (µT) of the magnetic field in the x-direction in the positions on the axis (z-axis) is more uniform in the range of z=−40 cm to +40 cm. The rate of change (dB(µT)/dz) in the z-direction of the distribution of B (µT) is found to be smaller than that of the (2), (3).

Figure 9:
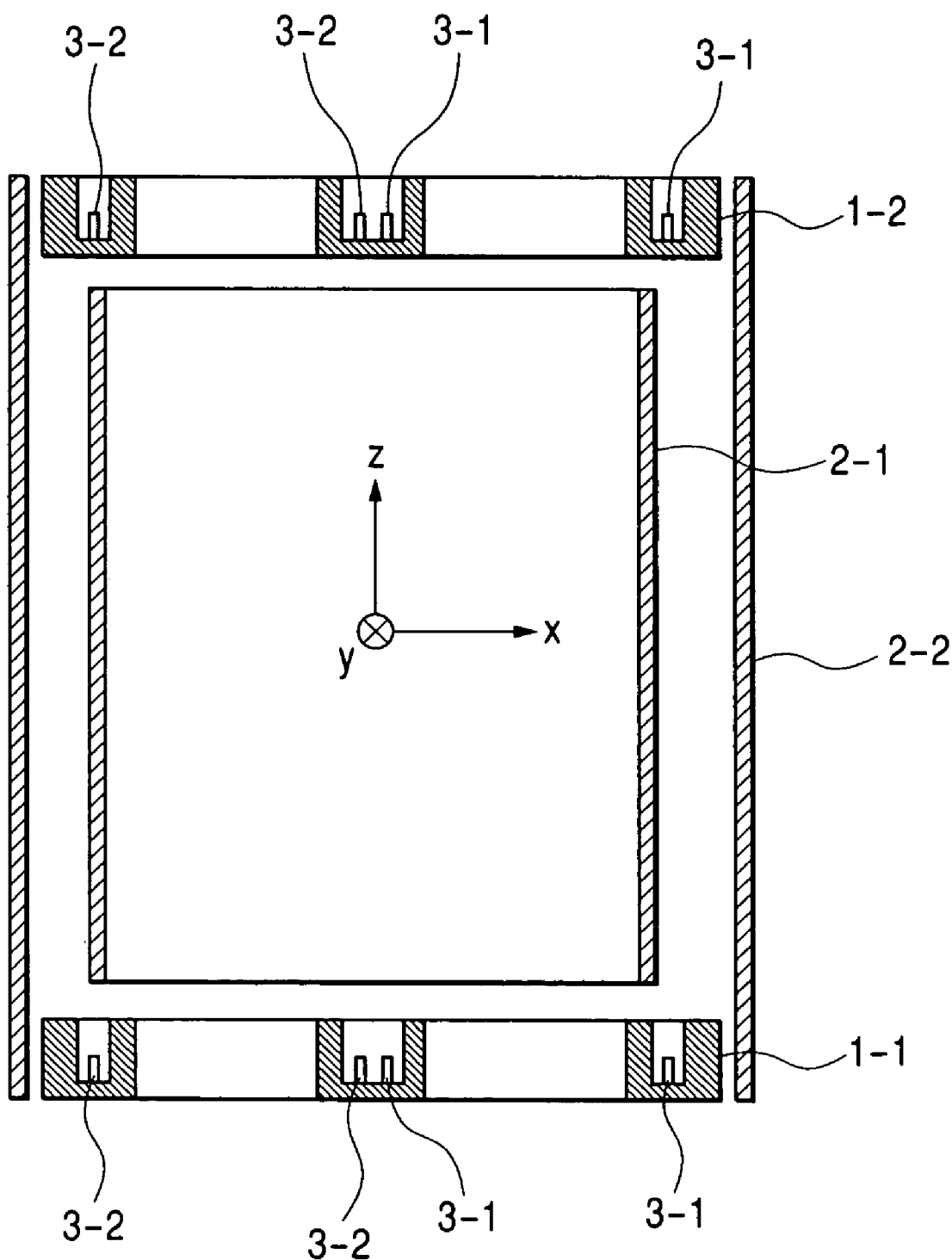
FIG. 9 is a cross-sectional view showing the construction of a magnetic shield used in an experiment of Embodiment 5 of the present invention.

FIG. 9 is a cross-sectional view showing the construction of a magnetic shield used in the experiment in Embodiment 5 of the present invention and is a cross-sectional view of xz plane. In the construction of the magnetic shield, superconducting loops are added to the magnetic shield constructed using the prior art magnetic shielding sheet. A cylindrical ferromagnetic substance 2-2 coaxial with an axis of a cylindrical ferromagnetic substance 2-1 is arranged on the outside of the cylindrical ferromagnetic substance 2-1. The cylindrical ferromagnetic substances 2-1, 2-2 are constructed using the prior art magnetic shielding sheets.

The diameter of the cylindrical ferromagnetic substance 2-1 is 73 cm and the length in the direction of the axis is 90 cm. The diameter of the cylindrical ferromagnetic substance 2-2 is 93 cm and the length in the direction of the axis is 120 cm. On the insides of the openings on both ends of the cylindrical ferromagnetic substance 2-2, the superconducting loops 3-1, 3-2 having semicircle shapes and constructed of high temperature superconducting wire, as shown in FIG. 6(A) are arranged in twos, respectively, along the direction of an external magnetic field (x-direction) so as to be symmetrical with respect to the axis of the cylindrical ferromagnetic substance. The superconducting loops 3-1, 3-2 are cooled by liquid nitrogen to maintain the superconducting state.

Figure 10:
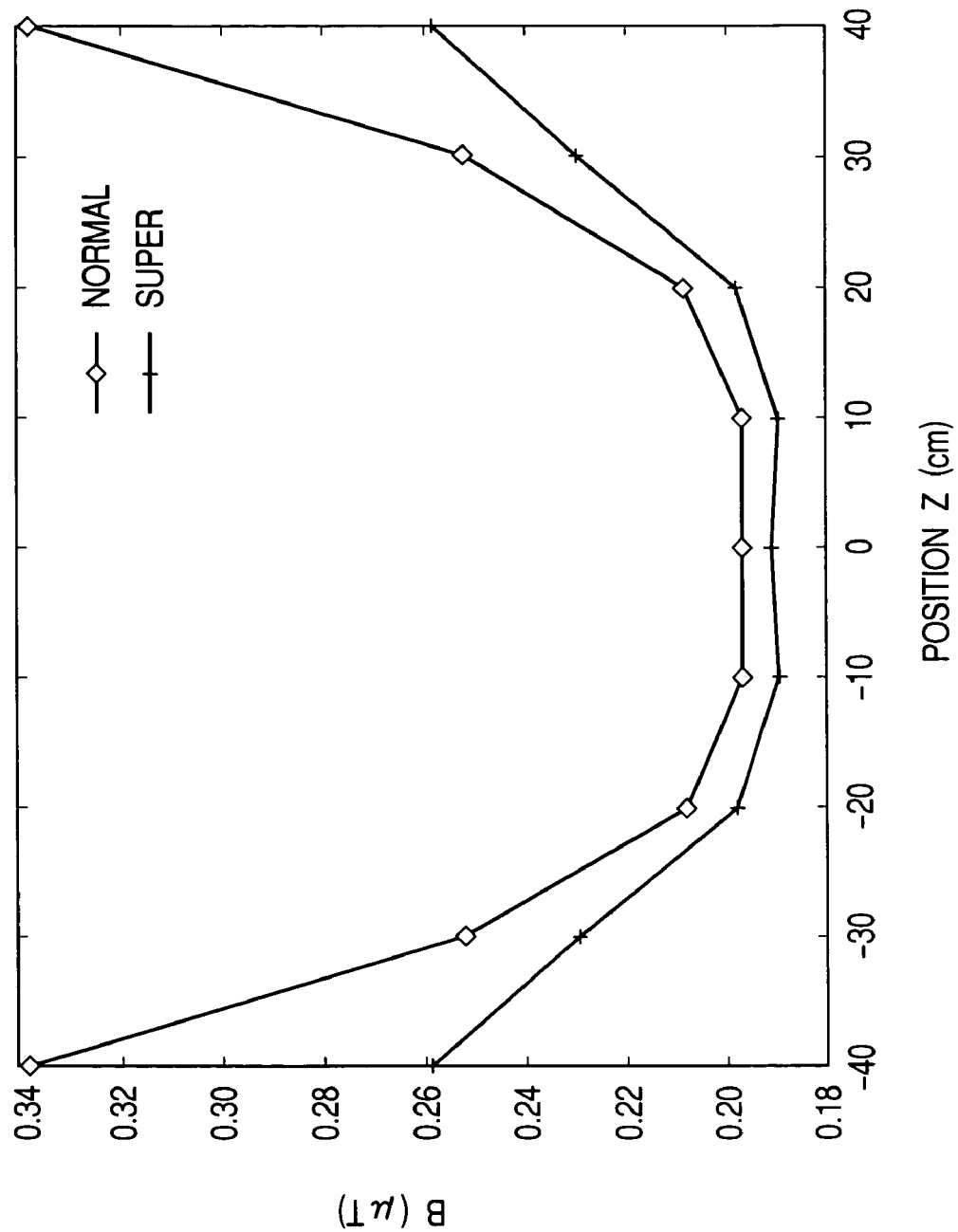
FIG. 10 is a diagram showing a result example of the experiment of Embodiment 5 of the present invention.

FIG. 10 is a result example in which with the center position in the direction of the axis (z-direction) of the magnetic shield shown in FIG. 9 as 0, magnitudes B (µT) of a magnetic field in the x-direction in the positions on the axis (z-axis) are obtained from an experiment. The magnitude of the external magnetic field in the x-direction in the center position of the magnetic shield shown in FIG. 9 is 13.2 µT. FIG. 10 shows the case of using the superconducting loops 3-1, 3-2 (super) and the case of not using the superconducting loops 3-1, 3-2 (normal).

From the results shown in FIG. 10, the shielding factor in the x-direction vertical to the axis (z-axis) is found to be improved. The shielding factor is defined by 20 log {(a magnitude of an external magnetic field applied in the x-direction)/(value B of the vertical axis shown in FIG. 10)}. The superconducting loops are combined with the cylindrical ferromagnetic substance to make possible the magnetic shield having a length shorter than that of the prior art cylindrical magnetic shield.

(Embodiment 6)

Figure 11:
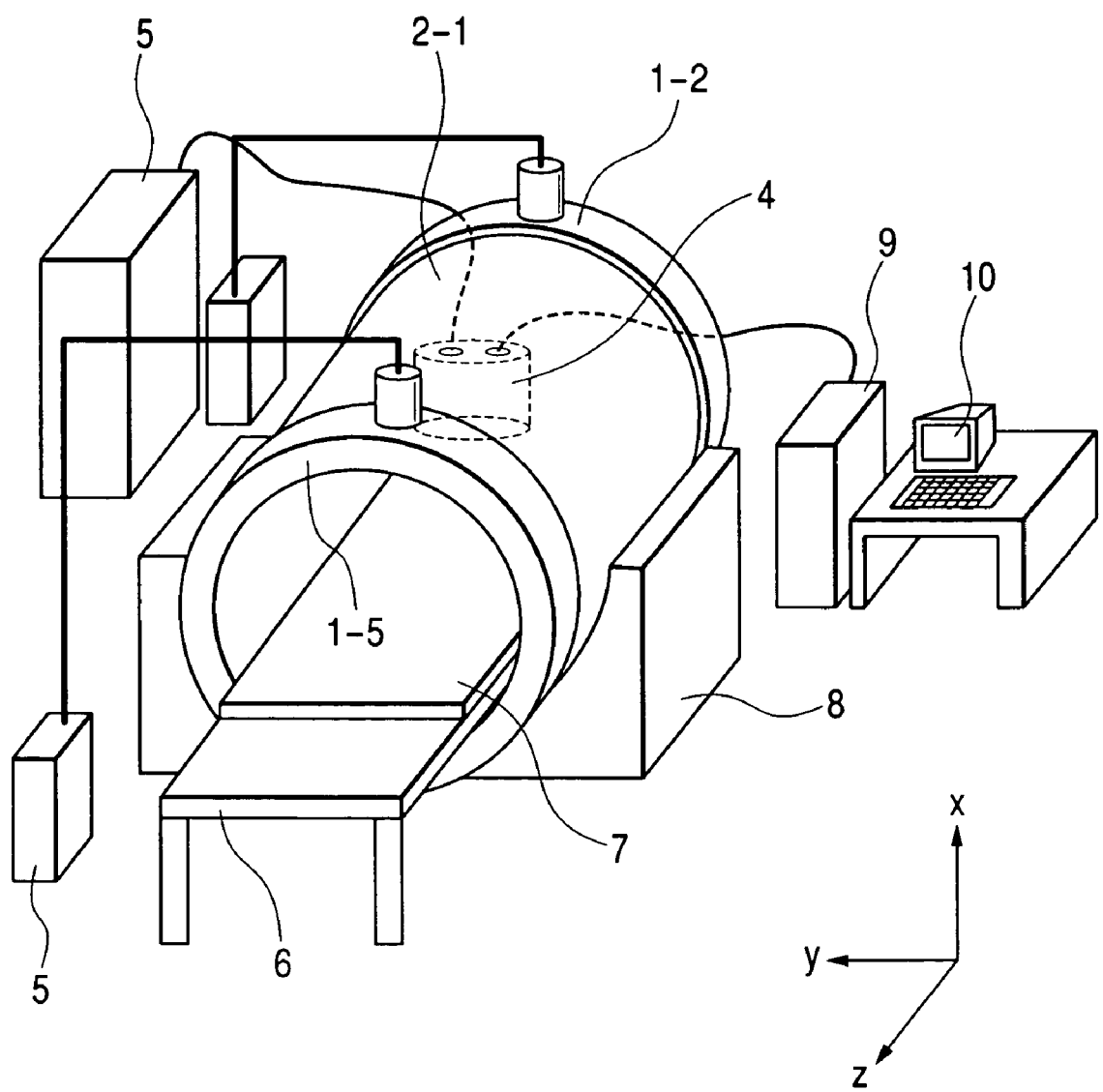
FIG. 11 is Embodiment 6 of the present invention and is a perspective view showing the construction of an instrument for measuring a biomagnetic field using the magnetic shield of the present invention.
Figure 12:
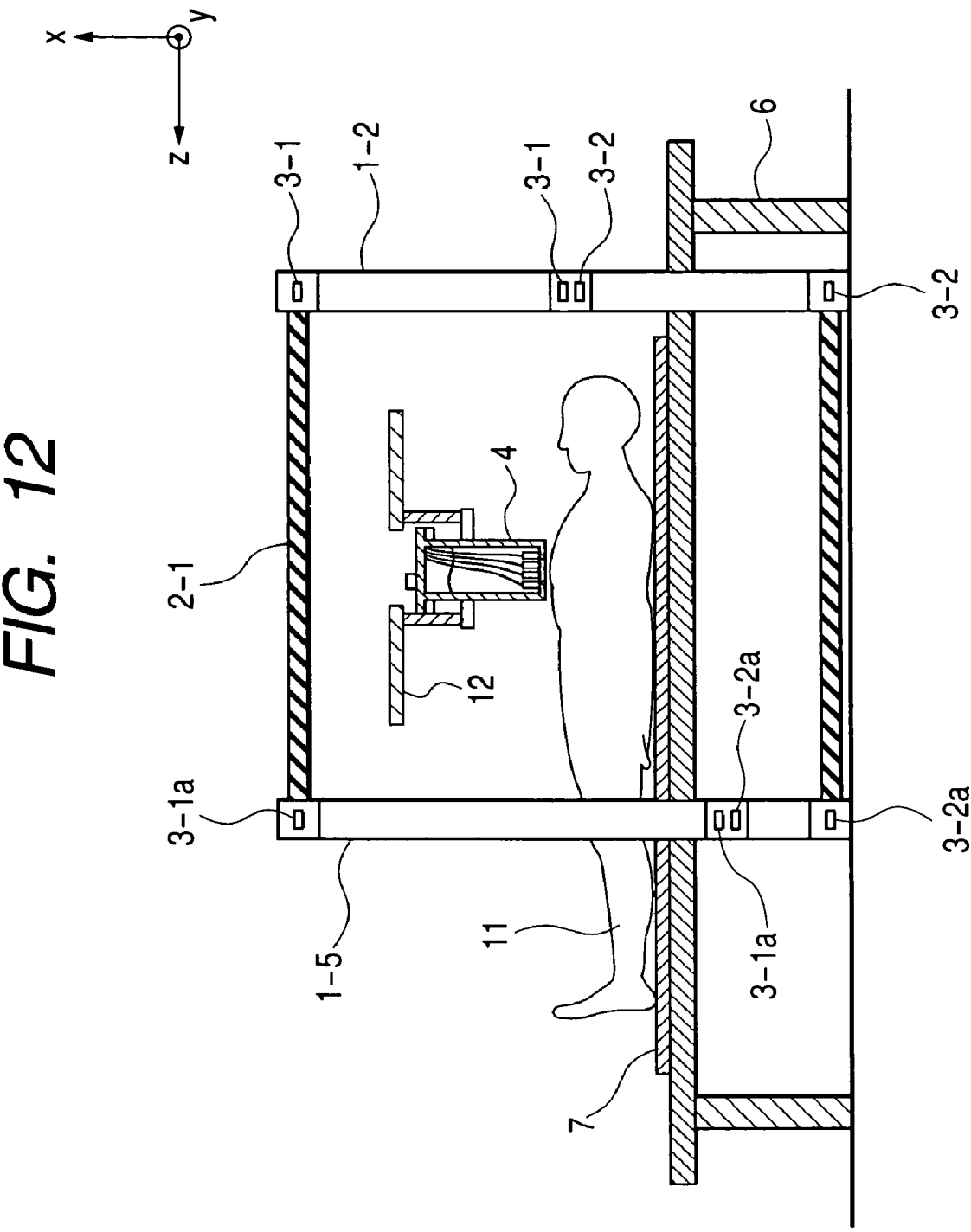
FIG. 12 is a cross-sectional view of the instrument for measuring a biomagnetic field of Embodiment 6 of the present invention.

FIG. 11 is Embodiment 6 of the present invention and is a perspective view showing the construction of an instrument for measuring a biomagnetic field using the magnetic shield of the present invention. FIG. 12 is a cross-sectional view of an instrument for measuring a biomagnetic field according to Embodiment 6 of the present invention and is a cross-sectional view of the plane (xz-plane shown in FIG. 11) passing through an axis of a cylindrical ferromagnetic substance. The instrument for measuring a biomagnetic field according to Embodiment 6 detects a biomagnetic field (hereinafter, simply called a magnetocardiogram (MCG)) generated from the heart of a living body. The magnetic shield is arranged so that the axis of the cylindrical ferromagnetic substance is substantially matched with the horizontal direction to the ground. The planes of detection coils of a plurality of fluxmeters are arranged in two dimensions in parallel to yz-plane in a dewar 4 so as to detect x-component of the MCG signal.

An environment magnetic field in the x direction is shielded by a cylindrical ferromagnetic substance 2-1 and superconducting loops 3-1a, 3-2a, 3-1 and 3-2. The superconducting loops 3-1a, 3-2a are housed in a superconducting loop container 1-5. The superconducting loops 3-1, 3-2 are housed in a superconducting loop container 1-2. The superconducting loops can reduce the x-component of environment magnetic field noise to detect the x-component of the magneto cardiogram at a high S/N ratio. The superconducting loops 3-1, 3-2 can also be omitted.

A subject 11 (living body) is placed on a movable plate 7 of a bed 6 in the inside of the cylindrical ferromagnetic substance 2-1. The position of a dewar 4 held by a gantry 12 is adjusted on the chest plane of the subject 11. The movable plate 7 movable in three directions of x, y and z with respect to the bed 6 optimizes the chest position to the dewar 4. The bed 6 and the movable plate 7 are constructed of nonmagnetic substances. The superconducting loops are cooled by a cryostat 5. The magnetic shield is held on the side surface of the cylindrical ferromagnetic substance 2-1 by a magnetic shield support base 8.

A data collection processing and sensor controller 9 drivingly controls the plurality of fluxmeters to collect and analyze magnetic field waveforms of the x-component of the measured MCG signal. The analyzed results are displayed on a display unit 10.

In the constructions shown in FIGS. 11 and 12, in place of the superconducting loops 3-1, 3-2, the net-like superconducting loop or the bulk-like high critical temperature superconductor shown in FIG. 6(F) can be used. In the examples shown in FIGS. 11 and 12, the superconducting loop containers 1-2, 1-5 are arranged on the outsides of the openings on both ends of the cylindrical ferromagnetic substance 2-1. They may be arranged on the insides of the openings on both ends of the cylindrical ferromagnetic substance 2-1. In the constructions shown in FIGS. 11 and 12, in place of the superconducting loops 3-1, 3-2, 3-1a and 3-2a, the two superconducting loops 3-1b, 3-2b shown in FIG. 6(D) can be used. In this case, the cross section of the magnetic shield is semicylindrical.

In the prior art instrument for measuring a biomagnetic field using the magnetic shield constructed of a cylindrical ferromagnetic substance, the length of the cylindrical ferromagnetic substance must be twice larger than the diameter of the opening of the cylindrical ferromagnetic substance. In the instrument for measuring a biomagnetic field according to Embodiment 6, the length of the cylindrical ferromagnetic substance can be shortened significantly. As a result, the openability to the subject is enhanced to increase the operability of the instrument of the measuring person.

(Embodiment 7)

Figure 13:
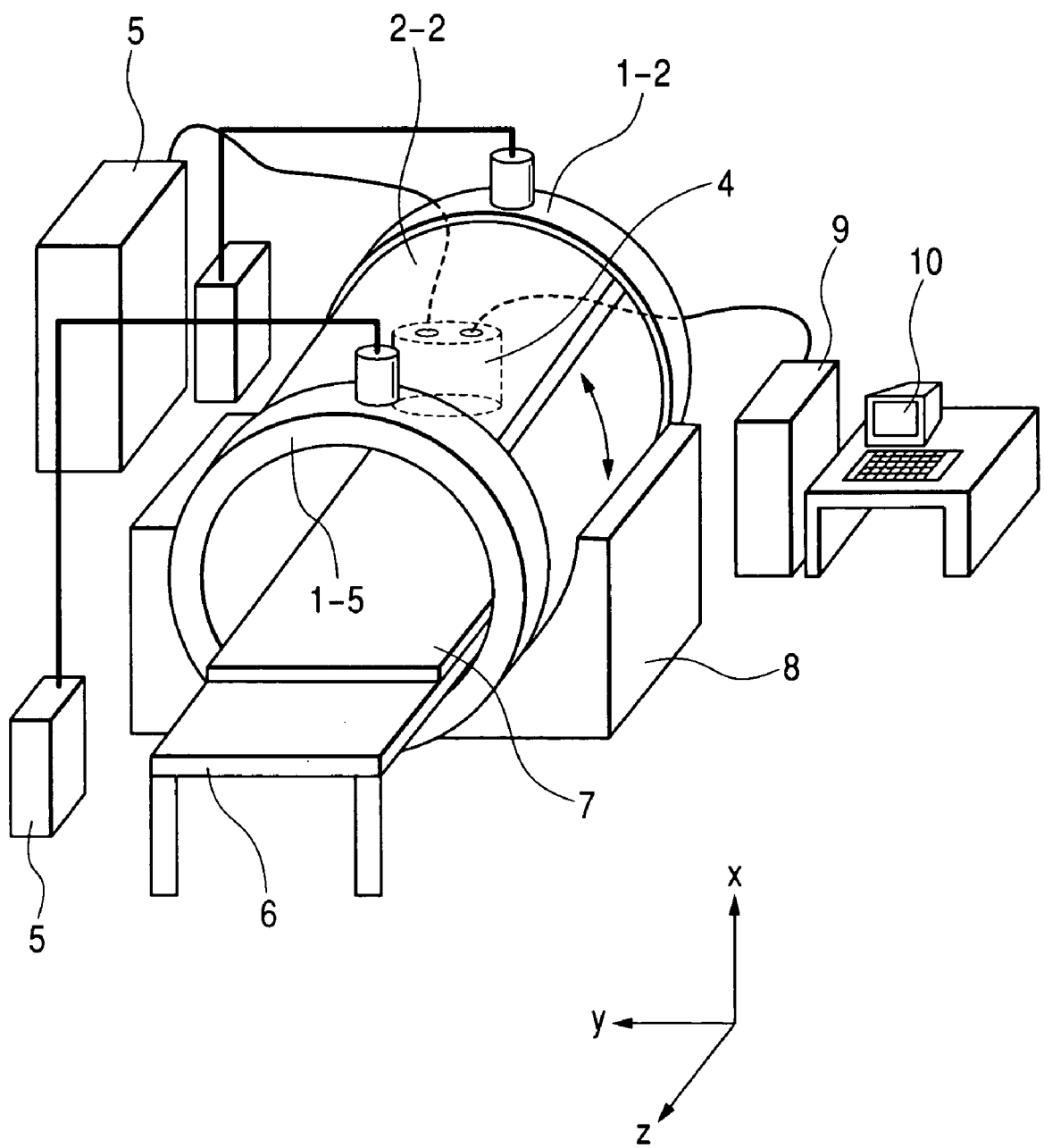
FIG. 13 is Embodiment 7 of the present invention and is a perspective view showing the construction of an instrument for measuring a biomagnetic field using the magnetic shield of the present invention.

FIG. 13 is Embodiment 7 of the present invention and is a perspective view showing the construction of an instrument for measuring a biomagnetic field using the magnetic shield of the present invention. The construction of the instrument for measuring a biomagnetic field according to Embodiment 7 is basically the same as that of the instrument for measuring a biomagnetic field according to Embodiment 6. A point different from the construction of the instrument for measuring a biomagnetic field according to Embodiment 6 will be described below.

A cylindrical ferromagnetic substance 2-1 coaxial with an axis of a cylindrical ferromagnetic substance 2-2 is arranged on the inside of the cylindrical ferromagnetic substance 2-2. The cylindrical ferromagnetic substances 2-1, 2-2 are divided into two parts, respectively, to be provided with a slide type open/close mechanism in the circumferential direction (indicated by the arrow) of the cylindrical ferromagnetic substances. Part of the cylindrical ferromagnetic substances 2-1, 2-2 can be opened and closed.

In the instrument for measuring a biomagnetic field according to Embodiment 6, the subject can go in and out and the instrument by the measuring person can be operated only at the opening part. In the instrument for measuring a biomagnetic field according to Embodiment 7, the subject can go in and out and the instrument by the measuring person can be operated at the side surface of the cylindrical ferromagnetic substance.

In the example shown in FIG. 13, the superconducting loop containers 1-2, 1-5 are arranged on the outsides of the openings on both ends of the cylindrical ferromagnetic substances 2-1, 2-2, respectively. They may be arranged on the insides of the openings on both ends of the cylindrical ferromagnetic substances 2-1, 2-2. As in Embodiment 6, superconducting loops 3-1, 3-2 can also be omitted.

In the Embodiment, the cylindrical ferromagnetic substance 2-1 can also be omitted.

(Embodiment 8)

Figure 14:
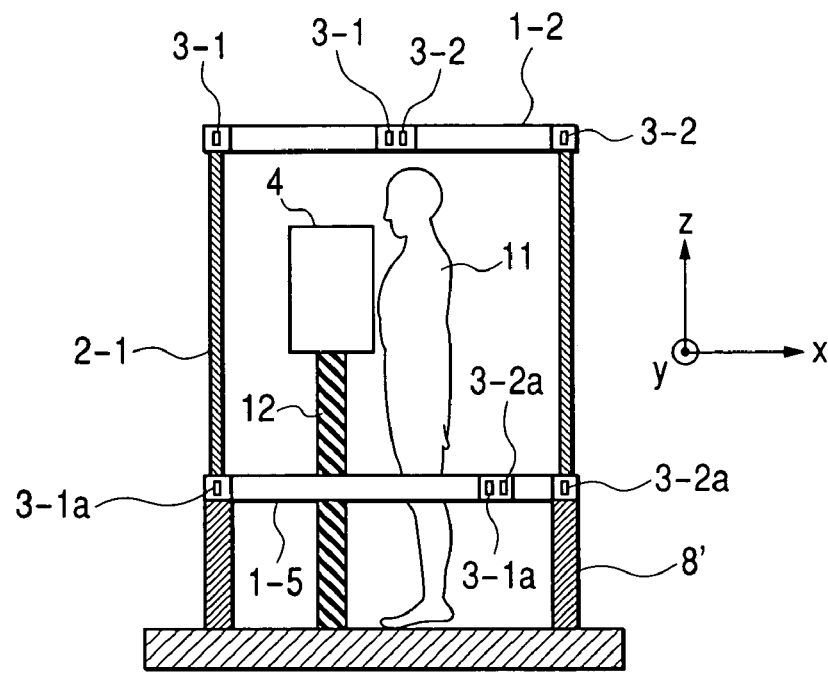
FIG. 14 is Embodiment 8 of the present invention and is a cross-sectional view showing the construction of an instrument for measuring a biomagnetic field using the magnetic shield of the present invention.

FIG. 14 is Embodiment 8 of the present invention and is a cross-sectional view showing the construction of an instrument for measuring a biomagnetic field using the magnetic shield of the present invention. The magnetic shield is arranged so that an axis of a cylindrical ferromagnetic substance is substantially matched with the direction vertical to the ground. The construction of the instrument for measuring a biomagnetic field according to Embodiment 8 is basically the same as that of the instrument for measuring a biomagnetic field according to Embodiment 6. A point different from the construction of the instrument for measuring a biomagnetic field according to Embodiment 6 will be described below.

In Embodiment 8, the magnetic shield used in Embodiment 6 is used to be placed vertically. The magnetic shield is held by a magnetic shield support base 8' on the plane orthogonal to the axis. A subject 11 in a standing posture is examined. The instrument for measuring a biomagnetic field according to Embodiment 8 is more simple in construction since the bed is unnecessary.

(Embodiment 9)

Figure 15:
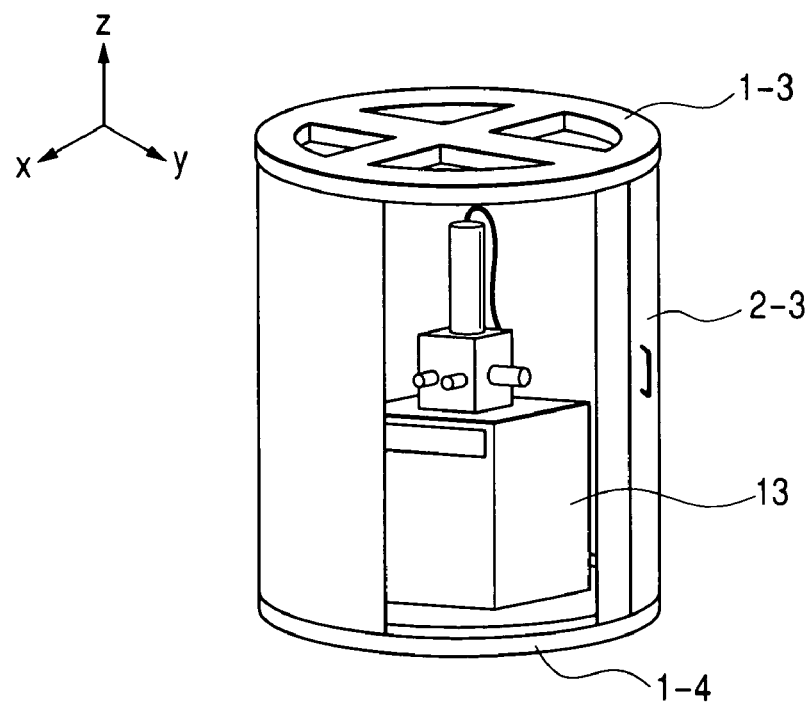
FIG. 15 is Embodiment 9 of the present invention and is a perspective view showing the construction of an electron microscope device using the magnetic shield of the present invention.

FIG. 15 is a perspective view showing the construction of an electron microscope device using the magnetic shield of the present invention. The magnetic shield is provided with an open/close mechanism slidable in the circumferential direction so that part of a cylindrical ferromagnetic substance 2-3 can be opened and closed. Four superconducting loops are housed in the respective insides of the superconducting loops 1-3, 1-4 arranged, respectively, adjacent the upper opening and the lower opening of the cylindrical ferromagnetic substance 2-3. The superconducting loops are constructed of high critical temperature superconducting wire. The four superconducting loops have quarter circle shapes and are arranged in x and y-directions so as to be symmetrical with respect to an axis of the cylindrical ferromagnetic substance 2-3.

An electron beam of an electron microscope 13 travels from the upper side to the lower side. The direction of the electron beam and the direction of an axis of the superconducting loops are parallel to each other. As in FIG. 4, the four superconducting loops are arranged in each of the open ends. Absorption of a magnetic field in the x and y-directions affecting the electron beam can be shielded. The magnetic shield shown in FIG. 15 can be used, not only in the electron microscope, but also in electronic drawing equipment.

In the conventional magnetically shielded room having a closed space manufactured of permalloy, air-conditioning equipment must be provided independently in the magnetically shielded room. In the construction of the magnetic shield shown in FIG. 15, when an electron microscope is installed in a clean room, air conditioning of the clean room flows air conditioned generally by downflow, which cannot interrupt the flow of the air.

The superconducting loops used in the above-described embodiments are formed of high critical temperature superconducting wire or bulk-like high critical temperature superconductors. As high critical temperature superconducting materials which become the superconducting state at a liquid nitrogen temperature, for example, $YBa_2Cu_3Ox$, $Bi_2Sr_2CaCu_2Ox$, $Bi_2Sr_2Ca_2Cu_3Ox$ or the like can be used.

In the cylindrical ferromagnetic substances used in the above-described embodiments and a tubular magnetic shield constructed of a ferromagnetic substance, one or more cylindrical ferromagnetic substances (or tubular ferromagnetic substances) can be formed using a known material. As such representative materials, it is possible to use, for example, a magnetic shielding sheet obtained by laminating the thin film of a high-permeability soft magnetic amorphous alloy (of Fe-B-Si-Cu, Co-Fe-Si-B, Co-Fe-Ni-Si-B, and Fe-Cu-Nb-Si-B) onto a polymer film.

In the magnetic shield of the present invention, the length in the direction of an axis can be shorter than that of the prior art cylindrical magnetic shield. From the result shown in FIG. 7 (FIGS. 9 and 10), in the example of the double cylindrical shield, when a biomagnetic field generated from a living body is detected at a minimum S/N ratio without using the superconducting loops of the present invention, the length in the direction of an axis of the double cylindrical shield must be above about 120 cm. When using the superconducting loops of the present invention, the length in the direction of the axis of the double cylindrical shield can also be about 100 cm to obtain an equal S/N ratio.

As described above, the present invention can realize the lightweight, small magnetic shield having high openability. In addition, cooling is easy since a number of superconductors are not used. The shielding current in response to external magnetic fields is naturally generated in the superconducting loops. A magnetic sensor for monitor monitoring external magnetic fields is unnecessary.

The present invention can provide a magnetic shield which can shield external magnetic fields in the direction of an axis of a tubular magnetic shield constructed of a ferromagnetic substance and in the direction vertical to the axis, and an instrument for measuring a biomagnetic field which permits measuring at a high S/N ratio using the same.

What is claimed is:

1. A magnetic shield comprising:
   a tubular magnetic shield constructed of a ferromagnetic substance for surrounding one axis; and
   a plurality of superconducting closed loops arranged on a plane vertical to said one axis near at least one end in the direction of said one axis of said tubular magnetic shield, the plurality of superconducting closed loops connecting with no power source.

2. The magnetic shield according to claim 1, wherein a plurality of said tubular magnetic shields having different diameters are arranged to surround said one axis.

3. A magnetic shield, comprising:
   a tubular magnetic shield constructed of a ferromagnetic substance for surrounding one axis;
   a plurality of superconducting closed loops arranged on a plane vertical to said one axis near at least one end in the direction of said one axis of said tubular magnetic shield; and
   a mechanism moving part of said tubular magnetic shield about said one axis, an opening part being formed in the circumferential direction of said tubular magnetic shield.

4. A magnetic shield, comprising:
   a cylindrical magnetic shield constructed of a ferromagnetic substance; and
   a plurality of superconducting closed loops arranged on a plane vertical to an axis near at least one end in the direction of said axis of said cylindrical magnetic shield, the plurality of superconducting closed loops connecting with no power source.

5. The magnetic shield according to claim 4, wherein a plurality of said cylindrical magnetic shields having different diameters are arranged to surround said axis.

6. A magnetic shield, comprising a cylindrical magnetic shield constructed of a ferromagnetic substance, and a plurality of superconducting loops arranged on a plane vertical to an axis near at least one end in the direction of said axis of said cylindrical magnetic shield,
   wherein a plurality of said cylindrical magnetic shields having different diameters are arranged to surround said axis,
   wherein the length in the direction of said axis of said cylindrical magnetic shield is longer as said diameter of said cylindrical magnetic shield is larger, and another said plurality of said cylindrical magnetic shields are arranged on the inside of said cylindrical magnetic shield in which said diameter is largest.

7. A magnetic shield, comprising a cylindrical magnetic shield constructed of a ferromagnetic substance, and a plurality of superconducting loops arranged on a plane vertical to an axis near at least one end in the direction of said axis of said cylindrical magnetic shield,
   wherein a plurality of said cylindrical magnetic shields having different diameters are arranged to surround said axis, the length in the direction of said axis of said cylindrical magnetic shield is longer as said diameter of said cylindrical magnetic shield is larger, another said plurality of said cylindrical magnetic shields are arranged on the inside of said cylindrical magnetic shield in which said diameter is largest, and said plurality of superconducting loops are arranged in the inside portion of said cylindrical magnetic shield arranged on the outermost side and in the outside portion of said cylindrical magnetic shield arranged on the innermost side.

8. The magnetic shield according to claim 7, wherein said plurality of superconducting loops have the same loop area and are arranged in the positions symmetrical with respect to said axis.

9. The magnetic shield according to claim 7, wherein said plurality of superconducting loops are constructed of first and second superconducting loops having the same loop area and arranged in the positions symmetrical with respect to said axis, and said first and said second superconducting loops have one straight line part and one arc part, respectively.

10. The magnetic shield according to claim 7, wherein said plurality of superconducting loops are constructed by first, second, third and fourth superconducting loops having the same loop area and arranged in the positions symmetrical with respect to said axis, and said first to said fourth superconducting loops have two straight line parts and one arc part, respectively.

11. The magnetic shield according to claim 7, further comprising a mechanism moving part of said plurality of cylindrical magnetic shields about said axis, an opening part being formed in the circumferential direction of said plurality of cylindrical magnetic shields.

* * * * *